United States Patent
Weststrate

(10) Patent No.: US 8,361,033 B2
(45) Date of Patent: *Jan. 29, 2013

(54) ACCESS NEEDLE WELL-SUITED FOR PERCUTANEOUS IMPLANTATION IN A BODY LUMEN

(75) Inventor: Patrice A. Weststrate, Norwood, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/114,462

(22) Filed: May 24, 2011

(65) Prior Publication Data

US 2011/0224619 A1    Sep. 15, 2011

Related U.S. Application Data

(63) Continuation of application No. 11/228,725, filed on Sep. 15, 2005, now Pat. No. 7,967,786.

(51) Int. Cl.
A61M 5/178    (2006.01)
(52) U.S. Cl. ......... 604/164.01; 604/164.03; 604/164.04; 604/175; 604/506
(58) Field of Classification Search ............ 604/164.01–170.03, 174, 175, 506
See application file for complete search history.

(56) References Cited

U.S. PATENT DOCUMENTS

| | | | |
|---|---|---|---|
| 4,861,334 A | 8/1989 | Nawaz | |
| 4,900,306 A | 2/1990 | Quinn et al. | |
| 5,112,310 A | 5/1992 | Grobe | |
| 5,122,122 A | 6/1992 | Allgood | |
| 5,167,627 A | 12/1992 | Clegg et al. | |
| 5,318,543 A | 6/1994 | Ross et al. | |
| 5,391,159 A | 2/1995 | Hirsch et al. | |
| 5,437,644 A | 8/1995 | Nobles | |
| 5,713,870 A | 2/1998 | Yoon | |
| 5,857,999 A | 1/1999 | Quick et al. | |
| 6,743,207 B2 | 6/2004 | Elbert et al. | |
| 2002/0165553 A1 | 11/2002 | Elbert et al. | |
| 2005/0027281 A1 | 2/2005 | Lennox | |

FOREIGN PATENT DOCUMENTS

WO    92/08513 A1    5/1992

*Primary Examiner* — Kevin C Sirmons
*Assistant Examiner* — Imani Hayman
(74) *Attorney, Agent, or Firm* — Kenyon & Kenyon LLP

(57) ABSTRACT

An access needle well-suited for percutaneous implantation in a body lumen, such as the stomach or the jejunum. In one embodiment, the access needle comprises a cannula, a needle, a retractable stopper and a spreader. The cannula is a tubular member having a proximal end, a distal end, a lumen and a pair of side windows providing access to the lumen. The needle is slidably mounted within the cannula lumen and comprises a needle stem and a needle handle, the needle stem having a proximal end, a distal end and a longitudinal lumen, the needle handle extending outwardly from the needle stem proximate to the proximal end thereof. The stopper is coupled to the needle stem for translational movement, the stopper comprising a pair of outwardly-biasing wings removably insertable through the side windows for engaging an interior surface of a patient. The spreader is mounted within the cannula and spreads the wings outwardly as the wings are inserted out the side windows.

20 Claims, 6 Drawing Sheets

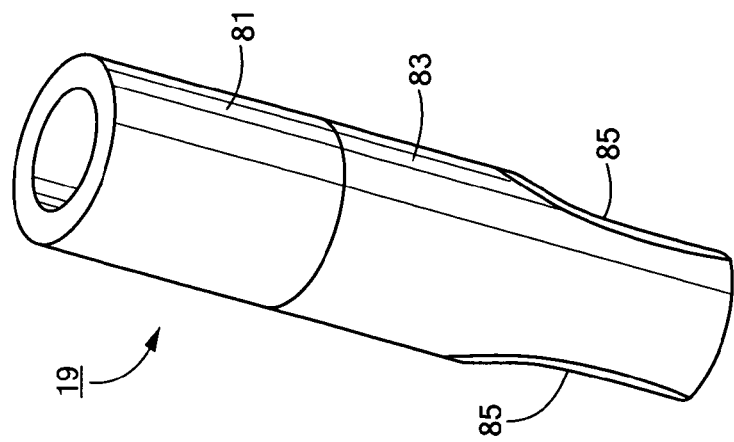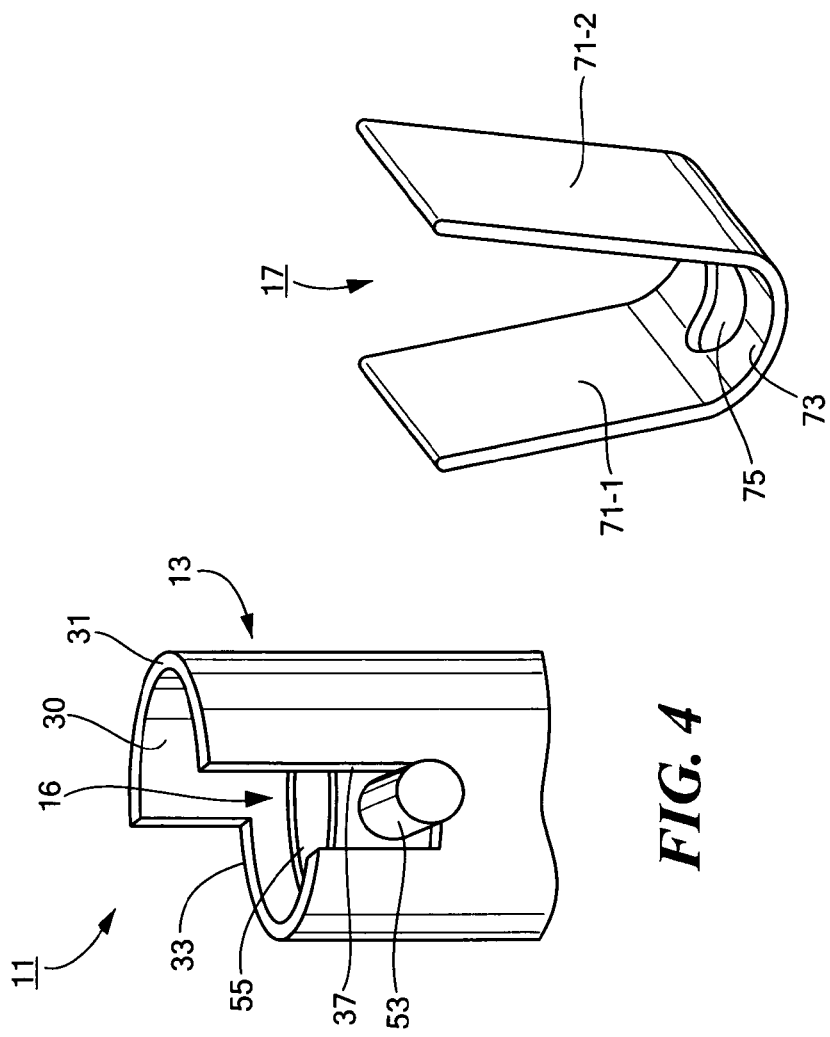

ACCESS NEEDLE WELL-SUITED FOR PERCUTANEOUS IMPLANTATION IN A BODY LUMEN

CROSS REFERENCE TO RELATED APPLICATION

This application is a continuation of U.S. Ser .No. 11/228,725, filed Sep. 15, 2005, which is hereby incorporated by reference in its entirety.

BACKGROUND OF THE INVENTION

The present invention relates generally to access needles of the type well-suited for percutaneous introduction into a body lumen and relates more particularly to a novel access needle that is well-suited for percutaneous implantation in a body lumen.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. Feeding is then typically performed by administering food through a catheter or feeding tube that has been inserted into the feeding tract, with the distal end of the feeding tube extending into the stomach and being retained therein by an internal anchor or bolster and the proximal end of the feeding tube extending through the abdominal wall.

(For certain patients, it is desirable for food to be administered directly to the patient's jejunum, without first passing through the patient's stomach. In such cases, a jejunostomy is typically performed, a jejunostomy being similar to a gastrostomy, except that a jejunostomy results in the distal end of the feeding tube being implanted in the patient's jejunum, instead of in the patient's stomach.)

Although gastrostomies were first performed surgically, most gastrostomies are now performed using percutaneous endoscopy and result in the implantation of a catheter/bolster assembly (also commonly referred to as a percutaneous endoscopic gastrostomy (PEG) device) in the patient. Two of the more common techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

According to the push method, the distal end of an endoscope is intubated (i.e., inserted) into a patient's mouth and is passed through the esophagus into the stomach. After distension of the stomach by inflation, an entry site on the abdomen is identified using the endoscope for transillumination, and an incision is made by passing the distal end of a needle coupled to an outer cannula through the abdominal and stomach walls and into the stomach. The proximal end of the outer cannula remains outside of the body and acts as a stop to prevent the proximal end of the needle from falling into the stomach. A snare is inserted into the stomach via the endoscope and is looped over the distal end of the needle. The snare is then "walked" up the needle until the outer cannula is snared. The snared cannula is then pulled proximally to tack the cannula to the stomach and, in turn, to secure the stomach wall to the abdominal wall. The needle is then removed while keeping the cannula in place. A first end of a flexible guidewire is then passed through the cannula and into the stomach where it is grasped by the snare, the second end of the guidewire remaining external to the patient. The endoscope and the snare are then withdrawn from the mouth of the patient to deliver the first end of the guidewire.

A push-type catheter implanting assembly is then inserted over the first end of the guidewire and is pushed over the guidewire towards its second end. The push-type catheter implanting assembly typically comprises a gastrostomy feeding tube, the gastrostomy feeding tube having a dome-shaped internal bolster disposed at its trailing end and having a tubular dilator serially connected to its leading end. The gastrostomy feeding tube and the internal bolster are typically made of a soft, biocompatible material, like silicone rubber, and may form a unitary structure. The dilator, which tapers in outer diameter from its trailing end to its leading end, is typically made of polyethylene or a like material which is stiffer than silicone but which still possesses some flexibility. Advancement of the push-type catheter implanting assembly over the guidewire continues until the front end of the dilator reaches the cannula and pushes the cannula out through the abdominal wall of the patient. The front end of the dilator is then pulled through the abdominal wall until the front end of the gastrostomy feeding tube emerges from the abdomen and, thereafter, the internal bolster at the rear end of the gastrostomy feeding tube engages the stomach wall. The guidewire is then removed from the patient. The clinician then re-intubates the patient with the endoscope and uses an optical channel in the endoscope to inspect whether the internal bolster is properly seated in the stomach.

If the internal bolster is properly placed against the stomach wall, a proximal portion of the implanted gastrostomy feeding tube is then typically cut and removed from the implanted tube to reduce the externally-extending portion of the tube to a desired length. (The removal of the proximal portion of the gastrostomy feeding tube also results in the removal of the dilator, which is connected thereto.) An external bolster is typically secured to the remaining implanted portion of the feeding tube to engage the abdomen in such a way as to prevent longitudinal movement of the feeding tube within the stoma tract. Additionally, a "Y-port" adapter is typically attached to the proximal end of the implanted feeding tube, the Y-port adapter being adapted to receive a pair of connector tips through which food and/or medications may be dispensed. In addition, a detachable locking clip is typically secured to the implanted feeding tube at a point between the external bolster and the Y-port adapter to prevent gastric fluids from escaping through the proximal end of the feeding tube when the feeding tube is not in use.

The pull method is similar in some respects to the above-described push method, the pull method differing from the push method in that, after the cannula is snared and the needle is removed therefrom, a first end of a suture is inserted through the cannula and into the stomach where it is grasped by the snare, the second end of the suture remaining external to the patient. The endoscope and the snare are then withdrawn from the mouth of the patient to deliver the first end of the suture. The first end of the suture is then coupled to the leading end of a pull-type catheter implanting assembly, the pull-type catheter implanting assembly typically comprising a gastrostomy feeding tube having an internal bolster at its trailing end and a plastic fitting at its leading end. The plastic fitting typically has a conical front portion that serves as a dilator, said conical front portion tapering in diameter from the leading end of the feeding tube to a front tip. A wire loop is fixed to the front tip of the plastic fitting, the first end of the suture being tied to the wire loop.

Using the second end of the suture, the pull-type catheter implanting assembly is then pulled retrograde through the patient until the gastrostomy feeding tube emerges from the abdomen of the patient and the internal bolster engages the stomach wall of the patient. Next, as is the case in the push method, the clinician then re-intubates the patient with the endoscope in order to visually inspect the placement of the internal bolster within the stomach. If the bolster is properly seated in the stomach, the implanted gastrostomy feeding tube is then typically cut to a desired length, an external bolster is typically secured to the cut implanted tube, a "Y-port" adapter is typically attached to the proximal end of the implanted feeding tube, and a detachable locking clip is typically secured to the implanted feeding tube at a point between the external bolster and the Y-port adapter.

Regardless of whether the push method or the pull method is used, an early part of the procedure involves using a needle/cannula assembly, also commonly referred to in the art as "an access needle." As explained above, the access needle is used to make an incision through the abdominal and stomach walls of the patient. A snare is then looped over the distal end of the needle portion of the access needle and is "walked" up the needle portion until the cannula portion of the access needle is snared. The snared cannula portion is then pulled proximally to tack the cannula portion to the stomach and, in turn, to secure the stomach wall to the abdominal wall. The needle portion of the access needle is then removed while keeping the cannula portion in place, and the distal end of a suture or guidewire is inserted through the cannula portion and into the stomach in order to be grasped by the snare.

One type of access needle commonly employed in the above procedure comprises a solid metal needle (or stylet) removably mounted within a metal cannula. A plastic needle hub is fixed to the proximal end of the metal needle, and a plastic cannula hub is fixed to the proximal end of the metal cannula. The needle hub and the cannula hub are sized and shaped to permit a portion of the needle hub to be removably inserted into the cannula hub in such a way as to delimit insertion of the needle distally through the cannula. A tab is provided on the needle hub and a corresponding slot is provided on the cannula hub, said slot being adapted to receive said tab in order to permit said needle and said cannula to be placed in a particular rotational orientation relative to one another. The cannula hub is also shaped to include a lateral flange upon which a user may rest, for example, his forefinger and middle finger.

Another type of access needle commonly used in the above procedure comprises a hollow metal needle removably mounted within a plastic cannula. A plastic needle hub is fixed to the proximal end of the metal needle, and a plastic cannula hub is fixed to the proximal end of the plastic cannula. The needle hub and the cannula hub are sized and shaped to permit a portion of the needle hub to be removably inserted into the cannula hub in such a way as to delimit insertion of the needle distally through the cannula.

In both of the above-described access needles, the lengths of the needle and the cannula are such that, with the needle fully inserted into the cannula, only the needle tip extends distally beyond the distal end of the cannula.

One type of problem periodically encountered with access needles of the types described above is the premature withdrawal or "backing-out" of the distal end of the access needle from the patient. As explained above, after the access needle is inserted into the patient, a snare is typically looped over the distal end of the needle and "walked" up the needle until the surrounding cannula is securely snared. As can readily be appreciated, if, prior to the secure grasping of the cannula by the snare, the patient moves relative to the access needle, the distal end of the access needle may be withdrawn from the patient. Such a withdrawal or "back-out" of the access needle from the patient is highly undesirable because, on one hand, it is exceptionally difficult to re-insert the access needle into the same incision holes already made in the abdominal and stomach walls, and, on the other hand, it is undesirable to make more incisions in a patient than are minimally required. Moreover, regardless of whether the needle is reinserted into the same holes or is used to make new incision holes, the re-introduced access needle must be located by the endoscope and grasped by the snare, all of which can be time-consuming and laborious. As a result, in order to avoid needle "back-out," it is not uncommon for a clinician other than the physician working the endoscope to hold the access needle securely against the skin of the patient until the cannula is fully snared. As can be appreciated, the involvement of a clinician in this manner means that an additional person is engaged in performing the procedure. The involvement of such an additional person is undesirable in that it increases the cost of performing the procedure and it makes more crowded the workspace in which the procedure is performed.

As can be appreciated, the above-described problem of access needle "back-out" is even greater where the access needle is used to perform percutaneous endoscopic jejunostomies since, in such a procedure, the needle must go deeper into tissue to locate the lumen of the jejunum and the procedure takes more skill to place the cannula.

SUMMARY OF THE INVENTION

It is an object of the present invention to provide a novel access needle that is well-suited for percutaneous introduction into a body lumen.

It is another object of the present invention to provide an access needle as described above that overcomes at least some of the problems identified above in connection with existing access needles.

Therefore, according to one aspect of the invention, there is provided an access needle comprising (a) a cannula, said cannula having a proximal end and a distal end; (b) a needle, said needle being disposed within said cannula and having a proximal end and a distal end, said distal end of said needle being adapted to extend distally beyond said distal end of said cannula; and (c) a retractable stopper, said retractable stopper being coupled to said needle for releasably anchoring said distal end of said needle within a patient.

According another aspect of the invention, there is provided an access needle comprising (a) a cannula, said cannula having a proximal end and a distal end; (b) a needle, said needle being slidably mounted within said cannula and having a proximal end and a distal end, said distal end of said needle being insertable into a patient; and (c) a releasable anchor for releasably anchoring the distal end of said needle within a patient.

According to yet another aspect of the invention, there is provided an access needle comprising (a) a cannula, said cannula having a proximal end, a distal end, a longitudinal lumen, and an opposing pair of side windows, said opposing pair of side windows being intermediately positioned between said proximal end and said distal end and providing access to said longitudinal lumen; (b) a needle, said needle comprising a needle stem slidably mounted within said longitudinal lumen of said cannula, said needle stem having a proximal end, a distal end and a longitudinal lumen, said needle stem being movable between a proximal position and a distal position, said distal end of said needle stem extending distally beyond said distal end of said cannula when said needle stem is in said distal position; and (c) a retractable stopper, said retractable stopper being mounted on said needle stem and coupled thereto for translational movement, said retractable stopper comprising a pair of outwardly-biasing wings removably insertable through said opposing pair of side windows for engaging an interior surface of a patient.

According to still yet another aspect of the invention, there is provided an access needle comprising (a) a cannula, said cannula having a proximal end, a distal end and a longitudinally-extending lumen; (b) a needle stem, said needle stem being hollow and having a proximal end and a distal end, said needle stem being slidably mounted within said longitudinally-extending lumen of said cannula and movable between a proximal position and a distal position, said distal end of said needle stem extending distally beyond said distal end of said cannula when said needle stem is positioned in said distal position; and (c) retractable means, engageable with an interior surface of a patient after said distal end of said needle stem has been inserted into a patient and said needle stem is positioned in said proximal position, for preventing said needle stem from being withdrawn from a patient.

The present invention is also directed to various techniques for using the aforementioned access needle.

For purposes of the present specification and claims, various relational terms like "top," "bottom," "proximal," "distal," "upper," "lower," "front," and "rear" are used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIG. 4 is a fragmentary perspective view of the access needle shown in FIG. 1, the access needle being shown with its needle in its distal position;

FIG. 5 is an enlarged perspective view of the stopper of the access needle of FIG. 1, the stopper being shown in its relaxed state;

FIG. 6 is an enlarged perspective view of the spreader of the access needle of FIG. 1;

DETAILED DESCRIPTION OF PREFERRED EMBODIMENTS

Figure 1:
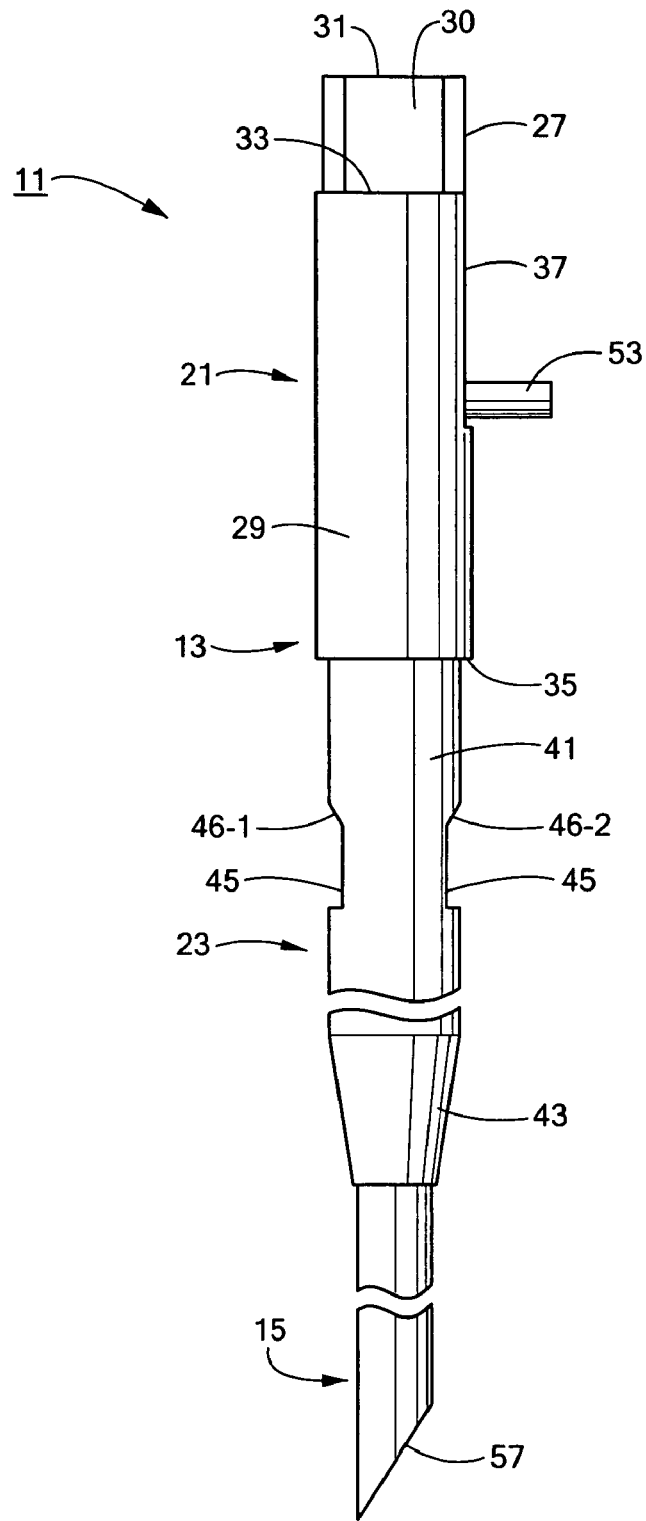
FIG. 1 is a fragmentary side view of one embodiment of an access needle constructed according to the teachings of the present invention, the access needle being shown with its needle in its distal position and its stopper in its retracted position.
Figure 2:
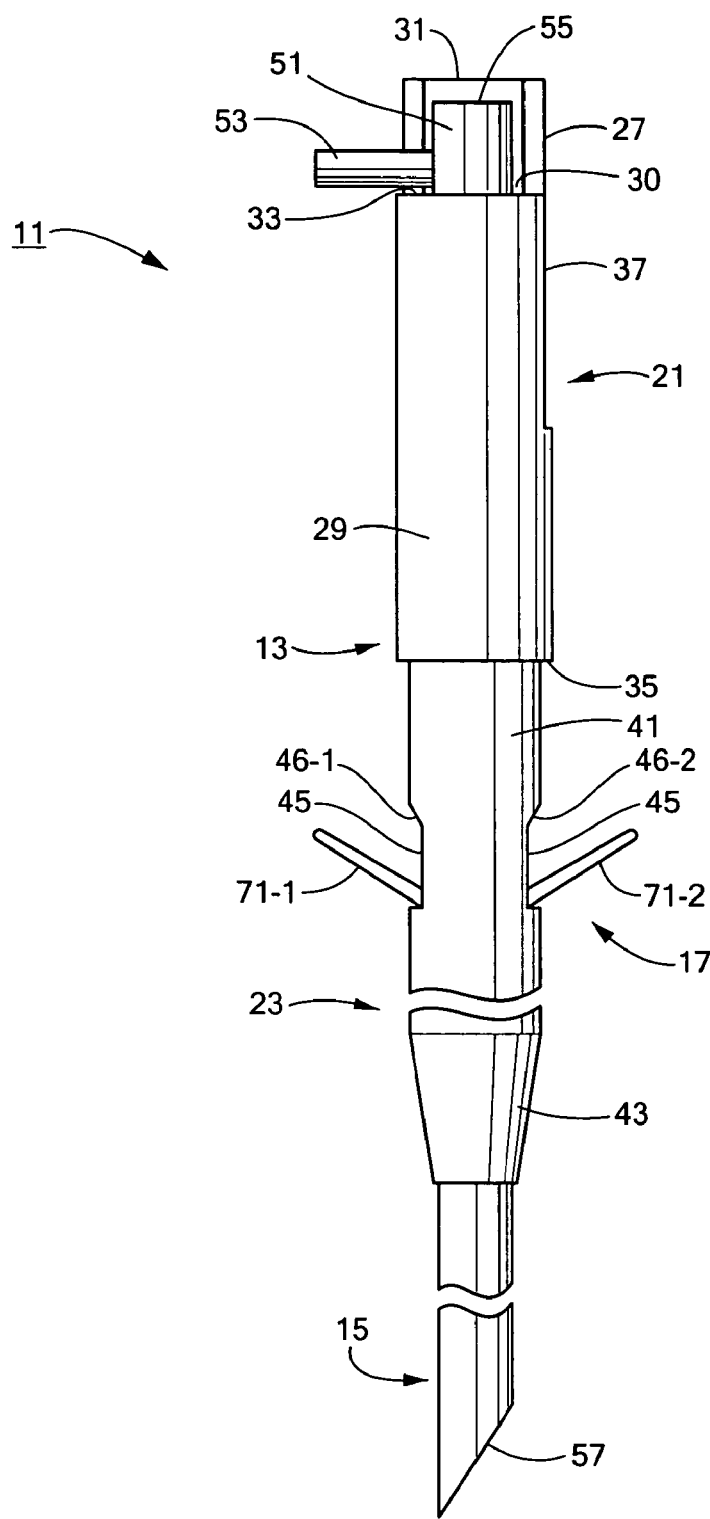
FIG. 2 is a fragmentary side view of the access needle of FIG. 1; the access needle being shown with its needle in its proximal position and its stopper in its extended position.
Figure 3:
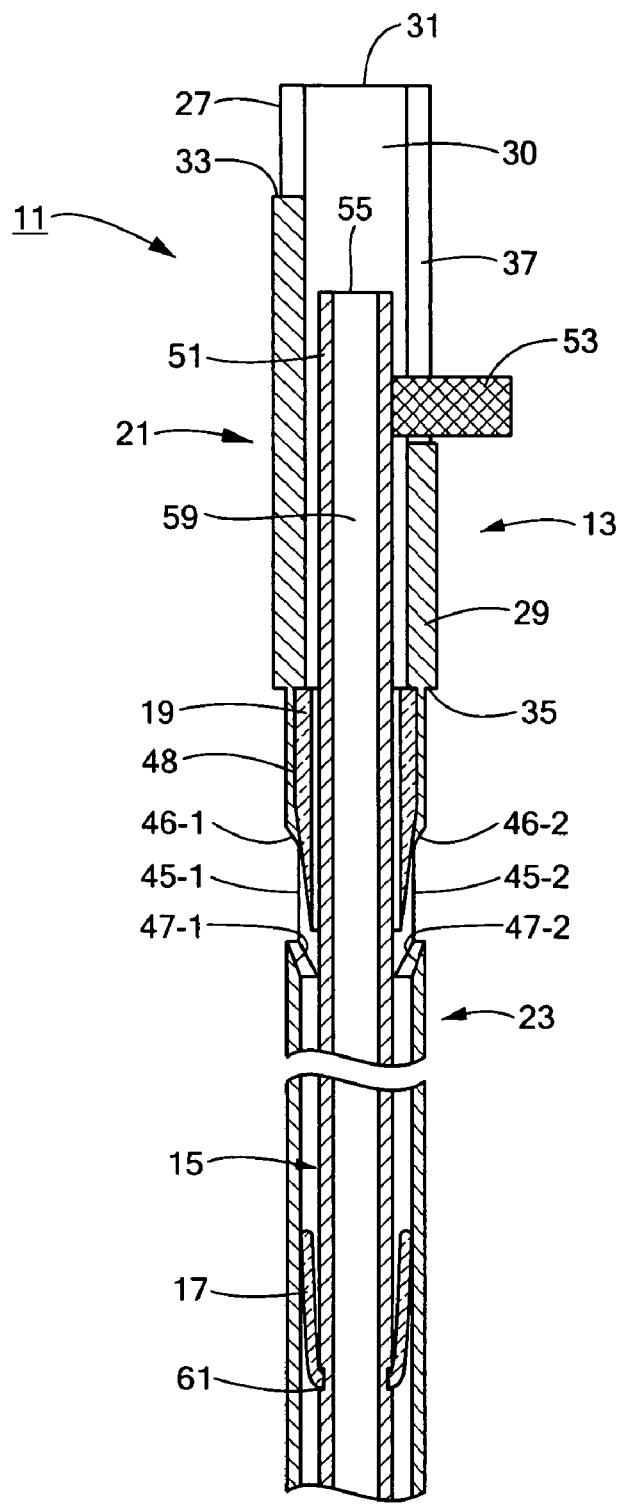
FIG. 3 is a fragmentary section view of the access needle of FIG. 1, the access needle being shown with its needle in its distal position and its stopper in its retracted position.

Referring now to FIGS. 1 through 4, there are shown various views of one embodiment of an access needle constructed according to the teachings of the present invention, said access needle being represented generally by reference numeral 11.

Access needle 11 includes a cannula 13, a needle 15, a stopper 17 and a spreader 19.

Cannula 13, which is preferably made of a biocompatible, rigid metal, such as stainless steel, is an elongated, unitary, tubular member shaped to include a proximal portion 21 and a distal portion 23. Proximal portion 21, in turn, is shaped to include a generally semi-annular proximal section 27 and a generally annular distal section 29, proximal section 27 and distal section 29 jointly defining a longitudinally-extending lumen 30. Proximal section 27 terminates proximally at a proximal end 31. Distal section 29 terminates proximally at a proximal end 33 and terminates distally at a distal end 35. A transverse slot 37 providing access to lumen 30 is provided in distal section 29 of proximal portion 21, slot 37 extending distally from proximal end 33 for a short distance before distal end 35. As will be discussed further below, when needle 15 is in its distal position, a portion of needle 15 is removably received in slot 37.

Distal portion 23 of cannula 13 is shaped to include a generally annular proximal section 41 and a funnel-shaped distal section 43, proximal section 41 and distal section 43 jointly defining a longitudinally-extending lumen 44 aligned with lumen 30. Proximal section 41, which extends distally from distal end 35 of proximal section 21, is coaxially aligned with proximal section 21 but has a reduced outer diameter for reasons to be discussed below. A pair of oppositely-facing side windows 45-1 and 45-2 are provided in proximal section 41, side windows 45-1 and 45-2 permitting the wings of stopper 17 to be removably inserted therethrough in the manner to be discussed further below. (Preferably, the proximal surfaces 46-1 and 46-2, respectively, and the distal surfaces 47-1 and 47-2, respectively, of windows 45-1 and 45-2 are angled as shown to facilitate the insertion and removal of the wings of stopper 17 through windows 45-1 and 45-2.) A recessed area 48 is provided along the inside surface of proximal section 41, recessed area 48 extending from the proximal end of proximal section 41 to a short distance before windows 45. As will be discussed further below, recessed area 48 is sized and shaped to receive the proximal portion of spreader 19 in such a fashion that spreader 19 does not move translationally within cannula 13.

Needle 15 comprises a needle stem 51 and a needle handle 53. Needle stem 51, which is slidably and rotatably mounted within cannula 13, is an elongated, unitary, tubular member preferably made of a biocompatible, rigid metal, such as stainless steel. Needle stem 51 is shaped to include a proximal end 55, a distal end in the form of a sharp, beveled tip 57 and a longitudinally-extending lumen 59. An annular recess 61 is provided on the outer surface of needle stem 51, recess 61 being sized and shaped to receive stopper 17 in such a fashion that needle stem 51 and stopper 17 are coupled together for translational movement within cannula 13 while permitting needle stem 51 to rotate relative to stopper 17.

Needle handle 53, which is an elongated, unitary, solid member, extends radially outwardly from needle stem 51 a short distance from proximal end 55. Needle handle 53 is preferably made of a biocompatible, rigid metal, such as stainless steel, and may be fixed to needle stem 51 by welding or the like. Needle handle 53 is appropriately dimensioned so that it may be received within slot 37 of cannula 13 or, alternatively, may be positioned on top of proximal end 33 of cannula 13. In this manner, when one wishes to place needle stem 51 in its distal position, handle 53 is aligned with and then drawn distally through slot 37. Alternatively, when one wishes to place needle stem 51 in its proximal position, handle 53 is removed from slot 37 and needle stem 51 is rotated until handle 53 may be placed upon proximal end 33 of cannula 13. (It should be appreciated that needle 15 could be modified to include a pair of needle handles, instead of a single needle handle 53; however, cannula 13 would need to be modified accordingly to accommodate both needle handles.)

In the present embodiment, needle 15 is dimensioned relative to cannula 13 so that, regardless of whether needle 15 is placed in its distal position or in its proximal position, tip 57 extends distally beyond cannula 13 (tip 57 extending further distally when needle 15 is in its distal position than when needle 15 is in its proximal position). However, it should be understood that needle 15 could be dimensioned relative to cannula 13 so that, when needle 15 is in its distal position, tip 57 extends distally beyond cannula 13 but when needle 15 is in its proximal position, tip 57 is withdrawn into cannula 13.

Stopper 17, which is also shown separately in FIG. 5, is a unitary, generally U-shaped clip made of spring steel, nitinol (a nickel/titanium alloy) or the like. Stopper 17 is shaped to include a pair of resilient, outwardly-biasing wings 71-1 and 71-2 interconnected by a base portion 73. (It should be understood that, whereas stopper 17 has a pair of wings 71-1 and 71-2, stopper 17 could be modified to include any number of wings.) As will be explained further below, wings 71-1 and 71-2 are appropriately dimensioned to be extendable through windows 45-1 and 45-2, respectively, in such a way as to engage an interior surface of a patient, thereby anchoring the distal ends of needle 15 and cannula 13 within the patient. A transverse opening 75 is provided in base portion 73 of stopper 17, opening 75 being sized so that, after inserting stopper 17 over needle 15, base portion 73 is securely retained within recess 61 of needle 15. In this manner, stopper 17 is fixed translationally, but not rotationally, relative to needle 15.

Spreader 19, which is also shown separately in FIG. 6, is a unitary, tubular member preferably made of rubber or the like. Spreader 19 is shaped to include a generally annular proximal portion 81 and a downwardly-tapered distal portion 83. Proximal portion 81 is appropriately dimensioned to be retained by an interference fit within recessed area 48 of cannula 13. Distal portion 83 of spreader 19 is appropriately dimensioned so that, when wings 71-1 and 71-2 of stopper 17 are moved proximally into alignment with windows 45-1 and 45-2, respectively, distal portion 83 engages and spreads wings 71-1 and 71-2 outwardly beyond their relaxed positions. As in the embodiment shown, distal portion 83 may be provided with a plurality of longitudinally-extending slots 85 to endow distal portion 83 with a certain degree of compressibility for when distal portion 83 is pressed against stopper 17.

Figure 7A:
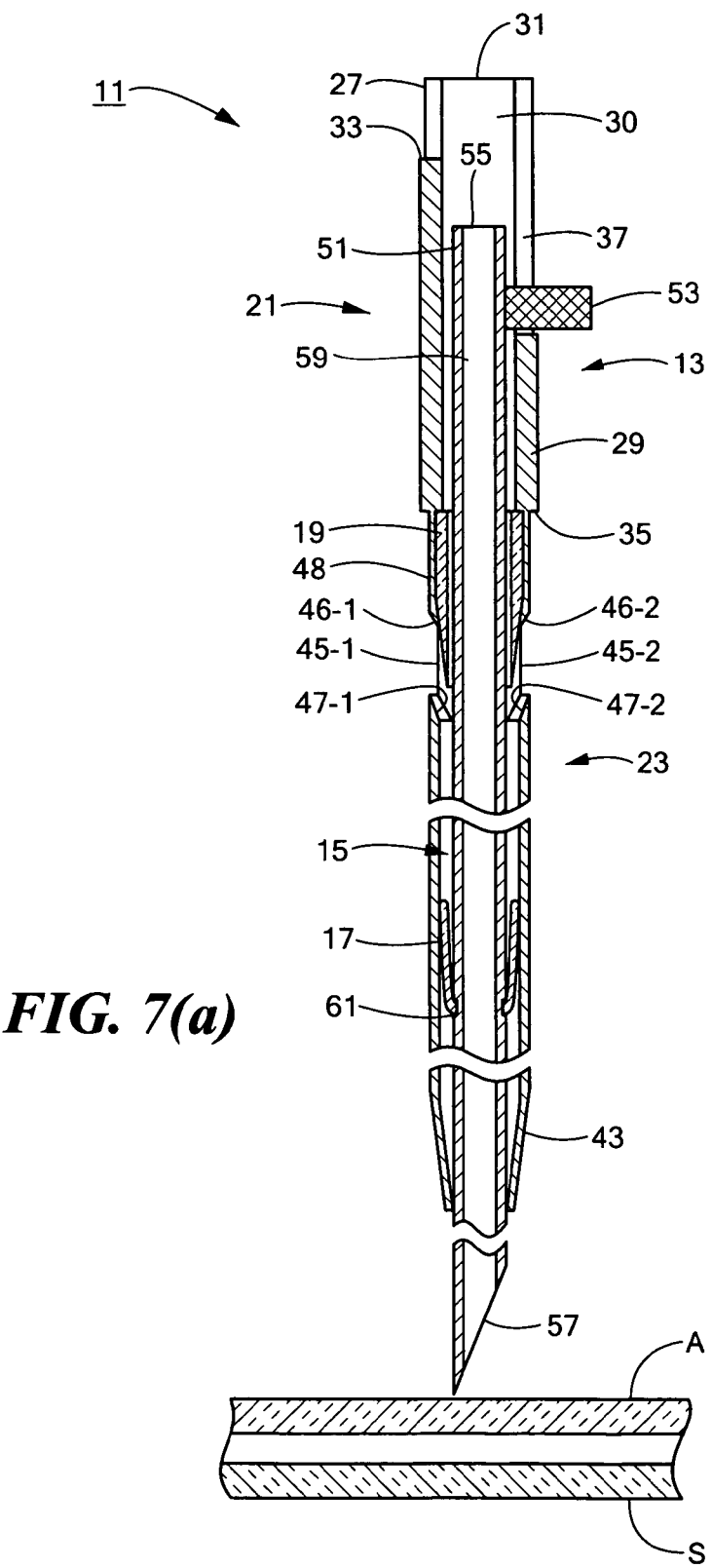
FIGS. 7(a) and 7(b) are fragmentary section views, showing the access needle of FIG. 1 being inserted into the stomach of a patient and, thereafter, being anchored within the stomach of the patient, respectively.

To prepare access needle 11 for insertion into a body lumen of a patient (such as into the stomach of a patient, as in FIG. 7(a), through the abdominal wall A and the stomach wall S of the patient), one first positions needle handle 53 as distally far as possible within slot 37. In so doing, needle 15 is moved distally relative to cannula 13, causing stopper 17 to be moved distally relative to windows 45-1 and 45-2 and to be compressed within cannula 13. Access needle 11, while in the aforementioned state, is then inserted into the patient.

Figure 7B:
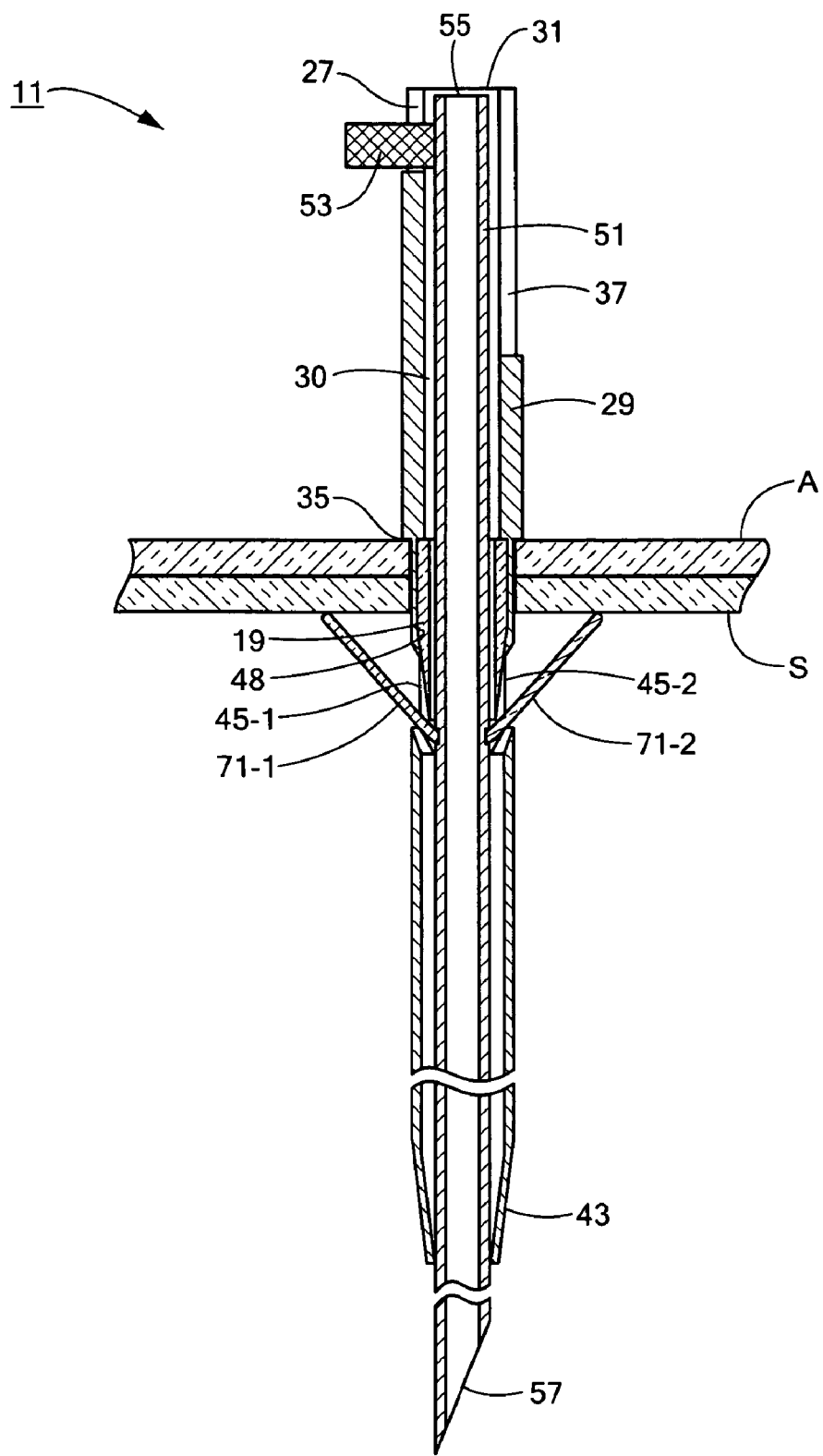

Referring now to FIG. 7(b), when one wishes to anchor access needle 11 within the body lumen of the patient, one moves needle 15 proximally relative to cannula 13 until needle handle 53 is removed from slot 37 and then rotates needle stem 51 approximately 180 degrees to rest needle handle 53 upon proximal end 33 of cannula 13. In so doing, wings 71-1 and 71-2 of stopper 17 are moved into engagement with spreader 19, spreader 19 causing wings 71-1 and 71-2 to be spread outwardly through windows 45-1 and 45-2, respectively. As can be seen, wings 71-1 and 71-2 engage an interior surface of the patient in an area surrounding the incision site, thereby impeding the withdrawal of access needle 11 from the patient. Preferably, the distance between distal end 35 and the free ends of wings 71-1 and 71-2 approximates the thickness of the patient's body traversed by access needle 11, thereby causing the body portion between distal end 35 and wings 71-1 and 71-2 to become entrapped therebetween.

To remove a thus-anchored access needle 11 from a patient, one merely rotates needle stem 51 relative to cannula 13 so that needle handle 53 is aligned with slot 37 and then distally advances needle 15 relative to cannula 13 so that needle handle 53 is moved as distally far as possible through slot 57 (see FIG. 7(a)). In so doing, stopper 17 is retracted sufficiently that wings 71-1 and 71-2 no longer extend through windows 45-1 and 45-2, respectively.

As can be appreciated, one benefit associated with access needle 11, as compared to existing access needles, is that only a single individual is needed to insert access needle 11 into a patient and then to anchor access needle 11 within the patient.

Where, as noted above, access needle 11 is implanted in the stomach of a patient as part of the early steps of a PEG procedure (or is implanted in the jejunum of a patient as part of the early steps of a PEJ procedure), once access needle 11 has been implanted in the manner discussed above, a guidewire or a suture may be passed into the stomach (or jejunum) through lumen 59 of needle 15. Consequently, as can be appreciated, another benefit of access needle 11 is that needle 15 need not be removed from cannula 13 in order for a guidewire or suture to be inserted into the patient. It should be noted, however, that access needle 11 may be used for purposes other than for use in PEG and PEJ procedures and that objects other than a guidewire or a suture may be delivered to a patient through lumen 59 of needle 15.

In another embodiment of the invention (not shown), access needle 11 is modified so that, instead of using needle handle 53, slot 37 and proximal end 33 to position needle 15 at its proximal and distal positions, a ratchet-type mechanism is employed, such a ratchet-type mechanism being capable of additionally positioning needle 15 at one or more intermediate positions between said proximal and distal positions.

In still another embodiment of the invention (not shown), access needle 11 may be modified by replacing stopper 17 with a balloon or expandable bladder that would be expanded by the operator with a syringe filled with air or water. The upper end of the needle would be wrapped with the air/water lines that lead to the bladder. Prior to inflation, the bladder would be compressed between the needle and cannula. Upon inflation, the bladder would expand out through openings in the cannula around the perimeter of the puncture to prevent the assembly from backing out. To remove the needle or cannula, the balloon would be deflated by the same means as inflation. The needle would be removed prior to the cannula since the pulling up on the needle would force any remaining bladder material up through the cannula and not disturb the incision site.

The embodiments of the present invention described above are intended to be merely exemplary and those skilled in the art shall be able to make numerous variations and modifications to it without departing from the spirit of the present invention. For example, it is to be understood that anchoring mechanisms, other than those disclosed, could be used and that anchoring mechanisms could be deployed with other types of actuators, such as a screw system. All such variations and modifications are intended to be within the scope of the present invention as defined in the appended claims.

What is claimed is:

1. A method of inserting an access needle into a patient comprising:
    using an access needle comprising:
        a cannula having a proximal end having a proximal end face, a distal end, a side window, and a longitudinally extending cannula lumen,
        a needle having a proximal end, a distal end, a longitudinally extending needle lumen, and a needle stem movably received within the cannula lumen, and
        a stopper attached to the needle stem;
    positioning the access needle in a first position by moving the needle distally relative to the cannula, wherein the stopper is located within the cannula lumen in the first position; and
    positioning the access needle in a second position by moving the needle proximally relative to the cannula and extending the stopper through the side window of the cannula.

2. The method of claim 1, wherein the cannula further comprises a slot at the proximal end, and said needle further comprises a needle handle at the proximal end, further comprising the step of: receiving the needle handle within the slot in the first position.

3. The method of claim 2, further comprising the step of: rotating the needle to remove the needle handle from the slot and rest the needle handle on the proximal end face of the cannula in the second position.

4. The method of claim 1, wherein in the first position the distal end of the needle extends from the distal end of the cannula, further comprising the step of:
    inserting the needle into the patient in the first position.

5. The method of claim 4, wherein in the second position the stopper engages an interior surface of the patient, further comprising the step of: retaining the needle in the patient in the second position.

6. The method of claim 5, further comprising inserting a suture or guidewire through the needle lumen in the second position.

7. The method of claim 5, further comprising removing the access needle from the patient in the first position.

8. The method of claim 1, wherein the stopper comprises resilient, outwardly biasing wings.

9. An access needle comprising:
    a cannula having a proximal end having a proximal end face, a distal end, at least one side window, and a longitudinally extending cannula lumen,
    a needle having a proximal end, a distal end, a longitudinally extending needle lumen, and a needle stem movably received within the cannula lumen, and
    a stopper attached to the needle stem, said stopper being receivable through the at least one side window of the cannula.

10. The access needle of claim 9, further comprising:
    a slot at the proximal end of the cannula; and
    a needle handle at the proximal end of the needle.

11. The access needle of claim 9, further comprising:
    a spreader disposed within the cannula lumen, said spreader comprising a unitary tubular member having an annular proximal portion and a tapered distal portion.

12. The access needle of claim 11, further comprising:
    a recessed area on the inner surface of the cannula, said recessed area located proximal to the at least one side window.

13. The access needle of claim 12, wherein said spreader is retained within the recessed area of the cannula by an interference fit.

14. The access needle of claim 11, wherein the distal tapered portion of the spreader engages the stopper to cause the stopper to extend through the at least one side window.

15. The access needle of claim 9, wherein the at least one side window comprises a pair of oppositely-facing side windows.

16. The access needle of claim 9, wherein the stopper comprises a U-shaped clip.

17. The access needle of claim 9, wherein the stopper comprises a base portion and at least one resilient wing.

18. The access needle of claim 17, further comprising:
    an annular recess in the outer surface of the needle; and
    an opening in the base portion of the stopper to receive the needle therein, wherein the opening is sized such that the base portion is retained within the annular recess.

19. The access needle of claim 9, wherein said stopper comprises a nickel-titanium alloy.

20. An access needle comprising:
    a cannula having a proximal end having a proximal end face, a distal end, at least one side window, and a longitudinally extending cannula lumen,
    a needle having a proximal end, a distal end, a longitudinally extending needle lumen, and a needle stem movably received within the cannula lumen, and
    a stopper attached to the needle stem, said stopper being receivable through the at least one side window of the cannula,
    wherein said stopper comprises an expandable bladder.

* * * * *